(12) United States Patent
Higuchi et al.

(10) Patent No.: US 7,973,027 B2
(45) Date of Patent: Jul. 5, 2011

(54) COMPOUND WITH ANTIMALARIAL ACTIVITY AND ANTIMALARIAL DRUG CONTAINING THE SAME AS ACTIVE INGREDIENT

(75) Inventors: Tsunehiko Higuchi, Nagoya (JP); Hirohisa Omiya, Inazawa (JP); Naoki Umezawa, Nagoya (JP); Hye-Sook Kim, Okayama (JP); Yusuke Wataya, Okayama (JP)

(73) Assignee: Nagoya City University, Nagoya-shi (JP)

( * ) Notice: Subject to any disclaimer, the term of this patent is extended or adjusted under 35 U.S.C. 154(b) by 180 days.

(21) Appl. No.: 12/224,387

(22) PCT Filed: Feb. 26, 2007

(86) PCT No.: PCT/JP2007/053537
§ 371 (c)(1),
(2), (4) Date: Apr. 2, 2009

(87) PCT Pub. No.: WO2007/097450
PCT Pub. Date: Aug. 30, 2007

(65) Prior Publication Data
US 2009/0275612 A1 Nov. 5, 2009

(30) Foreign Application Priority Data

Feb. 27, 2006 (JP) ................................. 2006-049678

(51) Int. Cl.
*A61K 31/47* (2006.01)
*C07D 215/46* (2006.01)
(52) U.S. Cl. ......................... 514/183; 546/162; 514/313
(58) Field of Classification Search ........................ None
See application file for complete search history.

(56) References Cited

OTHER PUBLICATIONS

Peter B. Madrid et al., "Incorporation of an Intramolecular Hydrogen-Bonding Motif in the Side Chain of 4-Aminoquinolines Enhances Activity against Drug-Resistant *P.falciparum*," J. Med. Chem. 2006, 49, pp. 4535-4543.
Kaylene Raynes et al., "Synthesis and Activity of Some Antimalarial Bisquinolines," J. Med. Chem. 1995, 38, pp. 204-206.
International Search Report mailed Mar. 20, 2007, issued on PCT/JP2007/053537.

*Primary Examiner* — Brandon J Fetterolf
*Assistant Examiner* — Craig Ricci
(74) *Attorney, Agent, or Firm* — Edwards Angell Palmer & Dodge LLP

(57) ABSTRACT

Compounds with high antimalarial activity; and antimalarial drugs containing the same as an active ingredient. There are provided compounds with antimalarial activity represented by the chemical formula: (wherein $R^1$ is H, Cl or $OCH_3$; $R^2$ is H or $CH_3$; $R^3$ is CH, $CH_2$, $C(CH_3)$, $CH(CH_3)$ or $C(CH_3)_2$; Ar is imidazole, triazole, pyridine, benzene, pyrrole, furan, thiophene or derivatives thereof; n is 1 to 5; and m is 1 to 5). Further, there are provided antimalarial drugs containing these compounds with antimalarial activity or pharmacologically acceptable salts thereof as active ingredients.

9 Claims, 8 Drawing Sheets

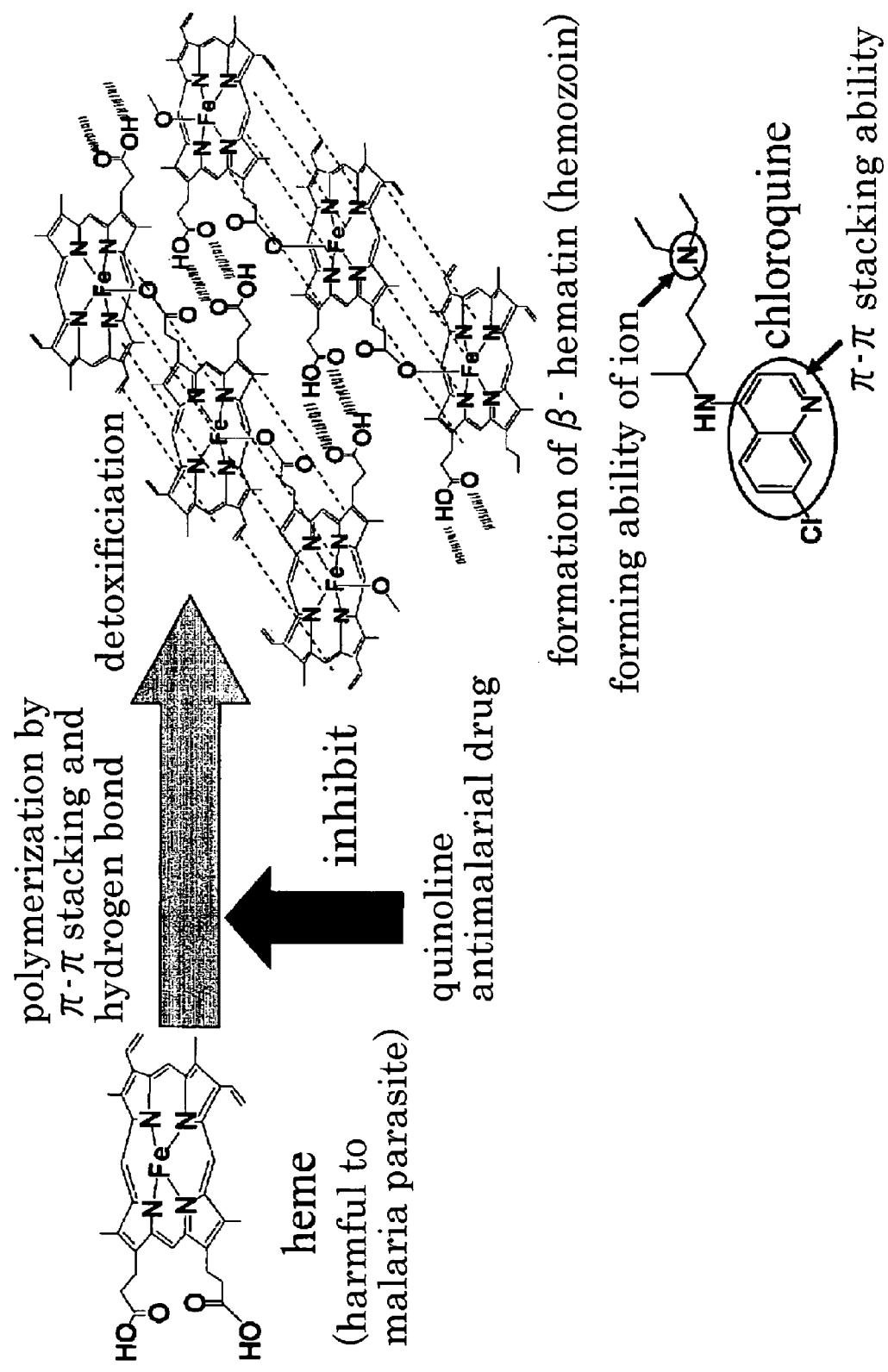
[Fig.1]

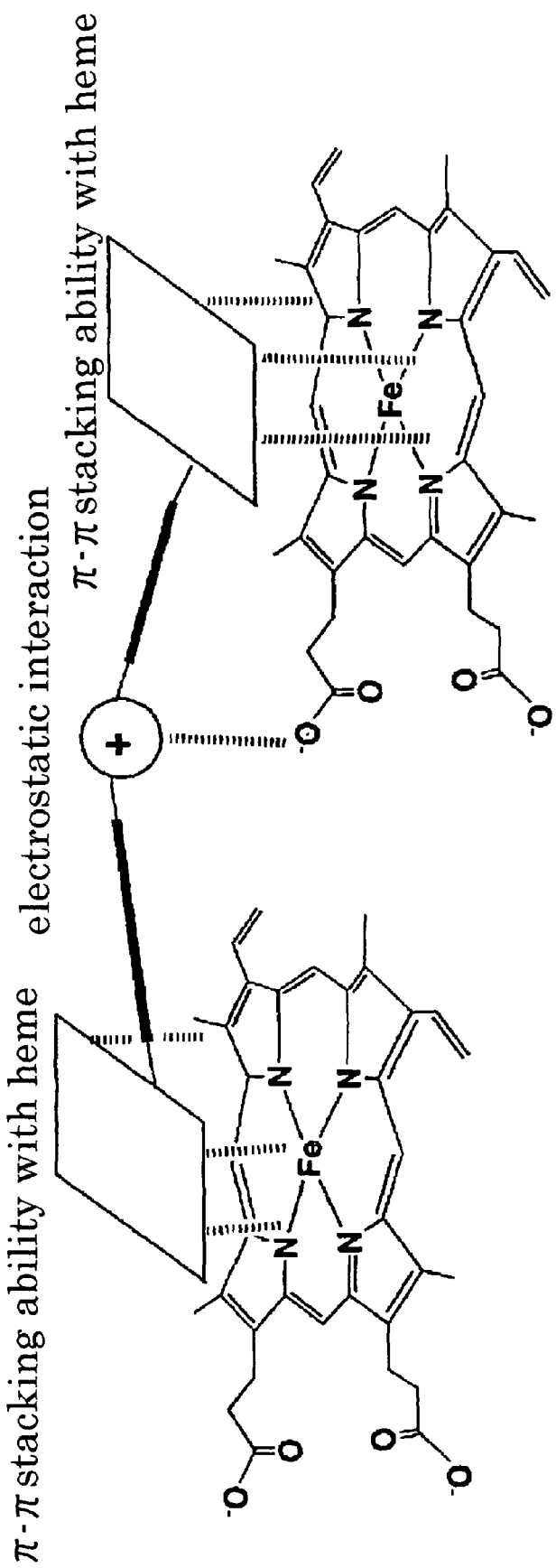
[Fig.2]

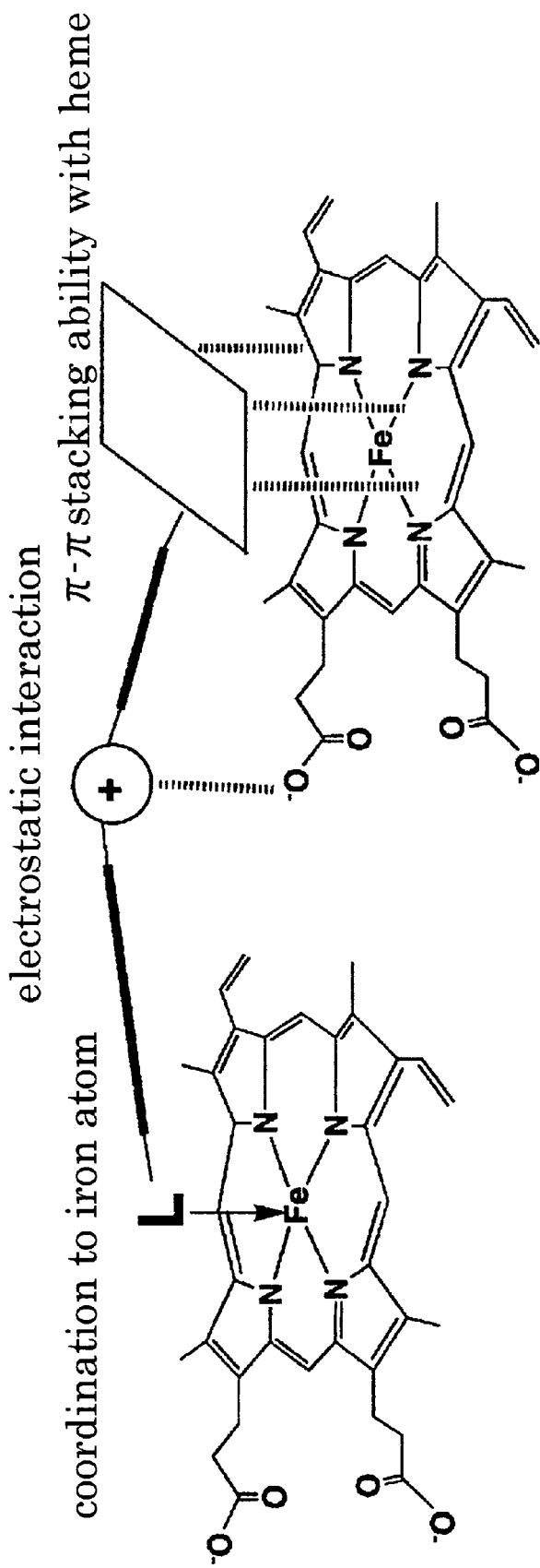
[Fig.3]

[Fig.4]
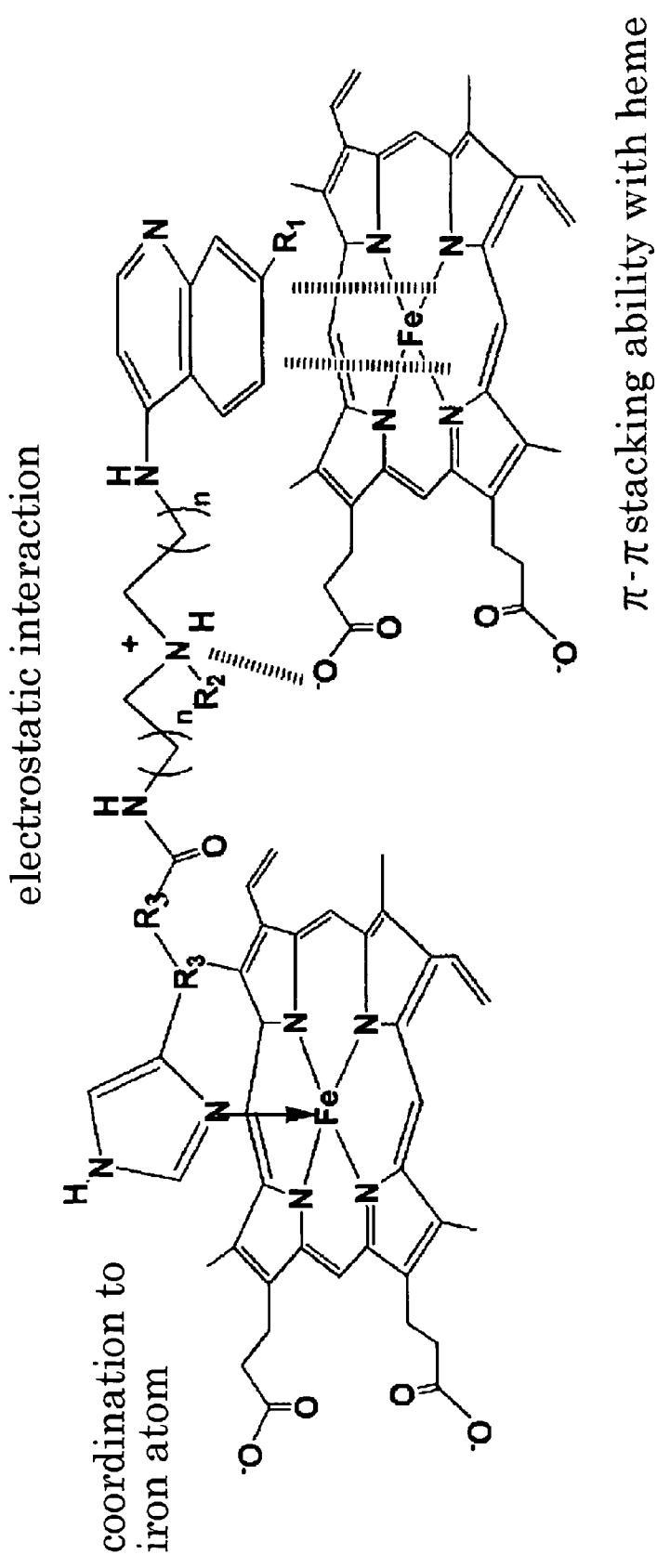

[Fig.5]
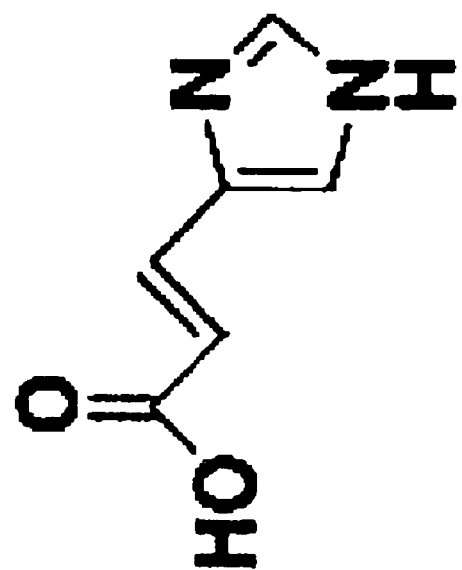 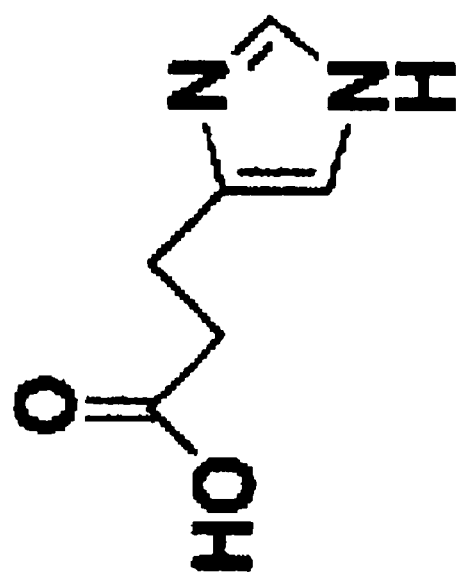

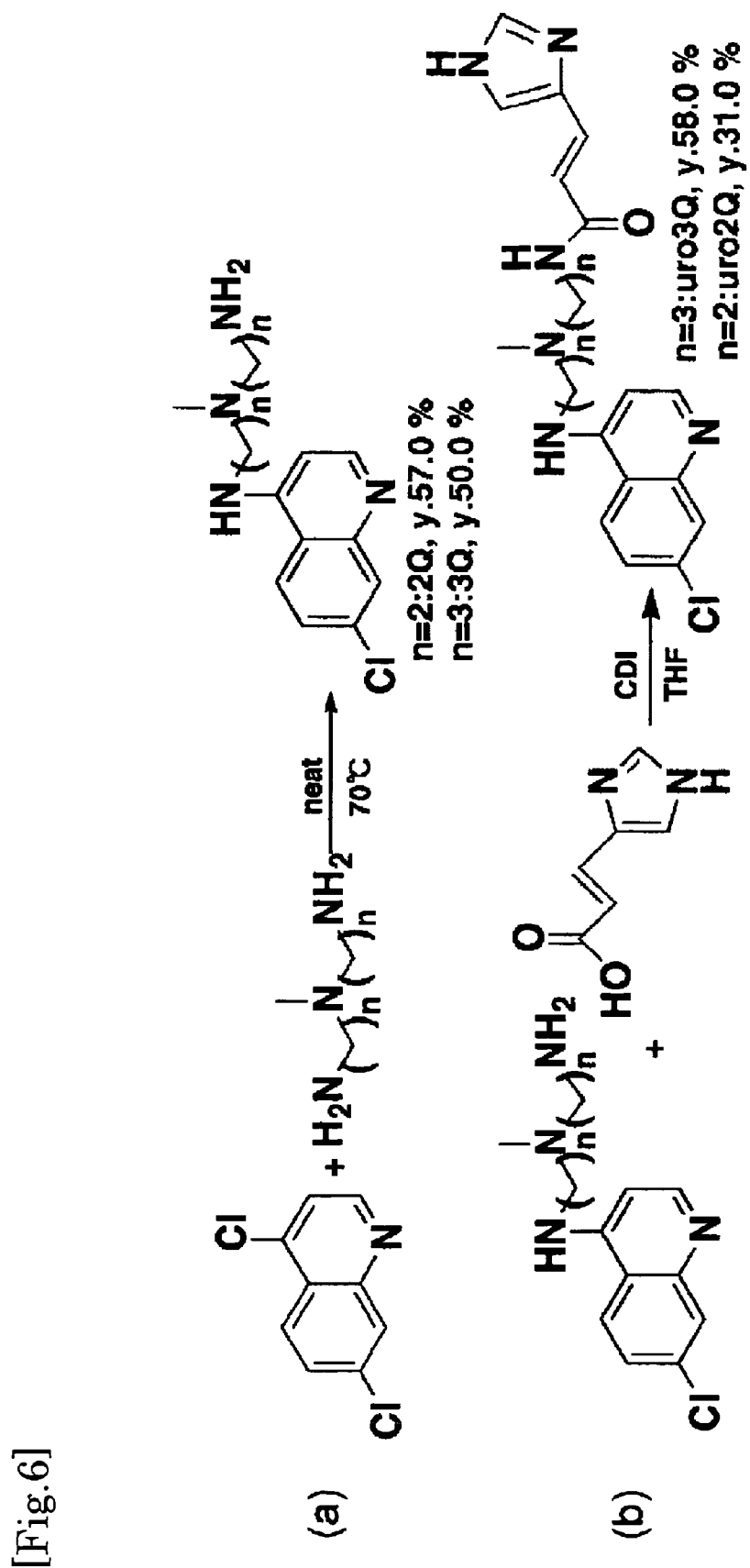
[Fig.6]

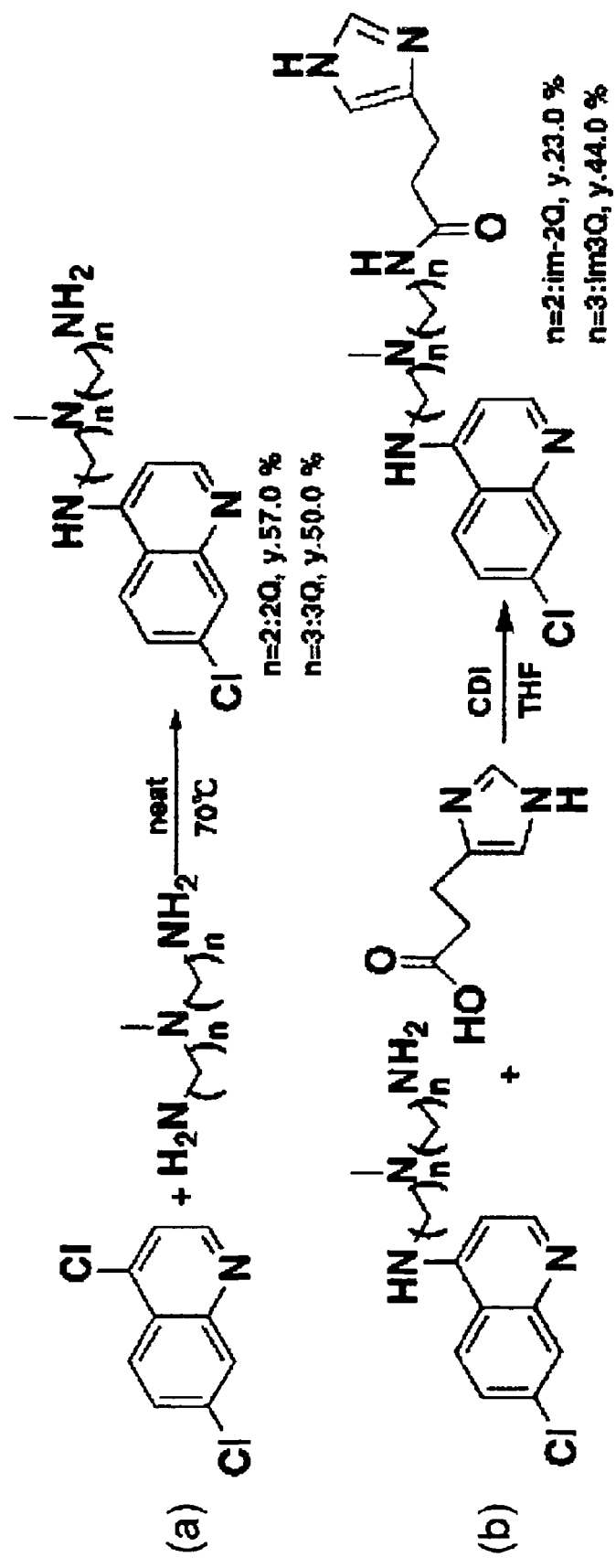
[Fig.7]

[Fig.8]

| Drug | EC$_{50}$(M) | | Selectivity |
|---|---|---|---|
| | P.falciparum*1 | FM3A cells*2 | |
| Chloroquine | $1.8 \times 10^{-8}$ | $3.2 \times 10^{-5}$ | 1780 |
| Quinine | $1.1 \times 10^{-7}$ | $1.0 \times 10^{-4}$ | 910 |
| Pyrimethamine | $1.0 \times 10^{-9}$ | $1.2 \times 10^{-7}$ | 120 |
| Mefloquine | $3.2 \times 10^{-8}$ | $2.9 \times 10^{-6}$ | 90 |
| Artemisinin | $1.0 \times 10^{-8}$ | $1.0 \times 10^{-5}$ | 1000 |
| uro-2Q | $6.6 \times 10^{-9}$ | $>3.0 \times 10^{-5}$ (96%) | >4545 |
| uro-3Q | $1.8 \times 10^{-7}$ | $>2.8 \times 10^{-4}$ (86%) | >1556 |
| im-2Q | $5.4 \times 10^{-7}$ | $>1.4 \times 10^{-4}$ (69%) | >259 |
| im-3Q | $3.1 \times 10^{-7}$ | $>6.4 \times 10^{-5}$ (69%) | >206 |

*1:P.falciparum,FCR-3 strain,*2: FM3A cell:mouse mammary tumor cell

COMPOUND WITH ANTIMALARIAL ACTIVITY AND ANTIMALARIAL DRUG CONTAINING THE SAME AS ACTIVE INGREDIENT

TECHNICAL FIELD

The present invention relates to a compound with antimalarial activity and use of the same.

BACKGROUND ART

Malaria is one of the most serious human infectious diseases caused by parasitic protozoa. It is estimated that several hundred million people are infected with malaria every year, of which several million people die. This threat has been continued since prehistoric times in the tropical zone. To date, main infection area has limited to the tropical zone and the subtropical zone. However, due to global warming, it is feared that malaria may extend to the temperate zone. In addition, together with spread of species that are resistant to conventional drugs, development of new effective medicines has been a pressing need.

Malaria parasites engulf and digest erythrocytes and take the protein thereof as a nutrient source. At this time, hemoglobin, heme, remained in the parasites is harmful to the parasites. Therefore, the parasites have a system for polymerizing heme and converting it into a sand-like form so as to carry out detoxification and excretion of the heme. It is thought that a quinoline antimalarial drug developed from quinine gains drug efficacy because it has an affinity to heme mainly on the basis of a π-π stacking ability and inhibits the polymerization of heme, thus making it impossible to carry out detoxification of harmful heme (see FIG. 1).

DISCLOSURE OF THE INVENTION

Problems to be Solved by the Invention

An object of the present invention is to provide a compound with high antimalarial activity and an antimalarial drug containing the same as an active ingredient. Another object of the present invention is to provide a treatment method and the like using the antimalarial drug.

Means to Solve the Problems

The present inventors have thought that designing and synthesizing of a molecule having a high affinity to heme could lead to creation of an antimalarial drug having a high efficacy, and have designed a molecule mentioned below. That is to say, the present inventors have got an idea that a functional group capable of interacting with heme is further introduced into a quinoline skeleton having a π-π stacking ability with respect to heme, thus largely enhancing the affinity to heme (see FIGS. 2 and 3). FIG. 2 shows design in which a molecule having a π-plane carrying out a π-π interaction with heme is further introduced into a quinoline ring via a linker such as amine having a positive charge. FIG. 3 shows design in which heterocycle and the like capable of being coordinated to heme iron is introduced in one side so as to strengthen the interaction with heme. Compounds with antimalarial activity designed by clearly considering the interaction with heme as mentioned above have not been reported to date. Thus, the design principle has a novelty. Both cases have a common point that a conjugated molecule is introduced into a quinoline ring via a linker.

Specifically, an aliphatic amino group is placed to a quinoline ring via a linker, and furthermore, aromatic carboxylic acid is subjected to dehydration condensation via a linker. Design is carried out so that a wide range of conjugated urocanic acids, imidazolopropinic acid that is known to have a strong coordination property, or the like, is linked (see FIG. 4), thus permitting strong interaction with heme simultaneously. A structural formula of a compound based on the above-mentioned design is shown below.

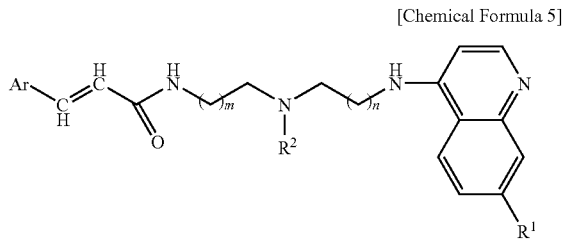

[Chemical Formula 5]

wherein R1 is H, Cl or OCH$_3$; R2 is H or CH$_3$; Ar is imidazole, triazole, pyridine, benzene, pyrrole, furan, thioiphene or derivatives thereof; n is 1 to 5; and m is 1 to 5.

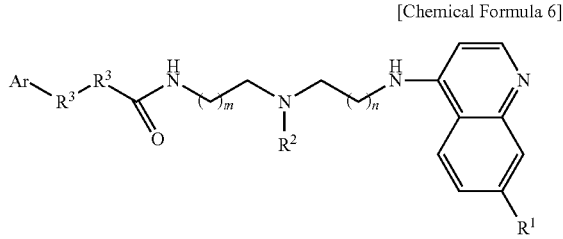

[Chemical Formula 6]

wherein R1 is H, Cl or OCH$_3$; R2 is H or CH$_3$; R3 is CH$_2$, CH(CH$_3$) or C(CH$_3$)$_2$; Ar is imidazole, triazole, pyridine, benzene, pyrrole, furan, thiophene or derivatives thereof; n is 1 to 5; and m is 1 to 5.

Synthesis is carried out according to the below mentioned scheme.

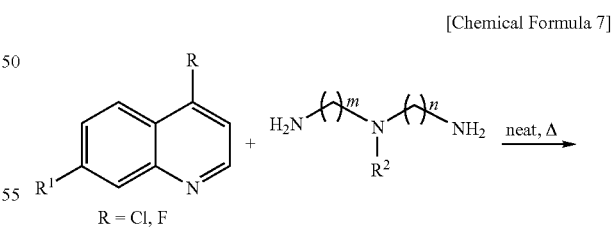

[Chemical Formula 7]

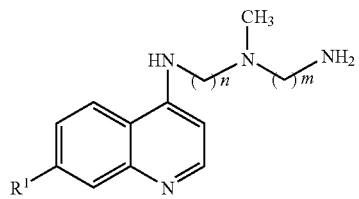

In this way, 4-haloquinoline derivative and triamines are heated in the absence of a solvent, and linked to each other by a nucleophilic substitution reaction, and dehydration condensation of a terminal amino group and a coordinating heterocycle-linked carboxylic acid such as imidazole is carried out. Thus, synthesis is carried out. This method has an advantage that the synthesis can be carried out in two stages.

As a result of the evaluation of the biological activities of the plurality of compounds synthesized by the above-mentioned method, it is clarified that the synthesized compounds generally have a low cytotoxicity and have middle level to extremely high level of antimalarial activities.

The present invention has made on the basis of the above-mentioned results and findings, and provides a compound with antimalarial activity, an antimalarial drug, and the like, as mentioned below.

[1] A compound with antimalarial activity represented by the following formula:

[Chemical Formula 8]

wherein R1 is H, Cl or OCH$_3$; R2 is H or CH$_3$; Ar is imidazole, triazole, pyridine, benzene, pyrrole, furan, thiophene or derivatives thereof; n is 1 to 5; and m is 1 to 5.

[2] The compound with antimalarial activity described in [1], which is represented by the following chemical formula:

[Chemical Formula 9]

wherein R1 is H, Cl or OCH$_3$; R2 is H or CH$_3$; R4 is H or CH$_3$; X is CH or N; n is 1 to 5; and m is 1 to 5.

[3] The compound with antimalarial activity described in [2], which is a compound selected from the group consisting of:
(1) a compound represented by the chemical formula, wherein R1 is Cl; R2 is CH$_3$; R4 is H; X is CH; n is 1; and m is 1; and,
(2) a compound represented by the chemical formula, wherein R1 is Cl; R2 is CH$_3$; R4 is H; X is CH; n is 2; and m is 2.

[4] A compound with antimalarial activity represented by the following formula:

[Chemical Formula 10]

wherein R1 is H, Cl or OCH$_3$; R is H or CH$_3$; R3 is CH$_2$, CH(CH$_3$) or C(CH$_3$)$_2$; Ar is imidazole, triazole, pyridine, benzene, pyrrole, furan, thiophene or derivatives thereof; n is 1 to 5; and m is 1 to 5.

[5] A compound with antimalarial activity described in [41] which is represented by the following formula:

[Chemical Formula 11]

wherein R1 is H, Cl or OCH$_3$; R2 is H or CH$_3$; R3 is CH$_2$, CH(CH$_3$) or C(CH$_3$)$_2$; R4 is is H or CH$_3$; X is CH or N; n is 1 to 5; and m is 1 to 5.

[6] The compound with antimalarial activity described in [51] which is:
(3) a compound represented by the chemical formula, wherein R1 is Cl; R2 is CH$_3$; R3 is CH$_2$; R4 is H; X is CH; n is 1; and m is 1; and
(4) a compound represented by the chemical formula, wherein R1 is Cl; R2 is CH$_3$; R3 is CH$_2$; R4 is H, X is CH; n is 2; and m is 2.

[7] An antimalarial drug including a compound with antimalarial activity according to any one of [1] to [6] or pharmaceutically acceptable salts thereof as an active ingredient.

[8] A prevention method or a treatment method of malaria, including administering an antimalarial drug described in [7] to a subject.

[9] Use of a compound with antimalarial activity described in any one of [1] to [6] for manufacturing an antimalarial drug.

BRIEF DESCRIPTION OF THE DRAWINGS

FIG. 1 shows a mechanism of action of a quinoline antimalarial drug. In main antimalarial drugs, the level of affinity to heme is related to the activity.

FIG. 2 shows design of a compound with antimalarial activity, which is expected to have a high affinity to heme. A molecule having a π-plane carrying out a π-π interaction with heme is linked to a quinoline ring via a material such as amine having a positive charge, thus largely enhancing the affinity to heme.

FIG. 3 shows design of a compound with antimalarial activity, which is expected to have a high affinity to heme. Heterocycle and the like capable of being coordinated is linked to a quinoline ring via a material such as amine having a positive charge so that three kinds of different actions (π-π stacking, electrostatic interaction, and coordination to an iron atom) are exhibited, thus largely enhancing the affinity to heme.

FIG. 4 shows design of a molecule that is expected to have a high affinity to heme. The molecule is designed so that π-π stacking by a quinoline skeleton, electrostatic interaction by an amino group, and coordination to an iron atom by an imidazole structure are carried out.

FIG. 5 shows a scheme for preparing a material of a novel compound: 3-(1H-Imidazol-4-yl)propionic acid.

FIG. 6 shows a scheme for synthesizing novel compounds (uro-2Q and uro-3Q).

FIG. 7 shows a scheme for synthesizing novel compounds (im-2Q and im-3Q).

FIG. 8 is a table showing the evaluation results of the novel compounds. The novel compounds are compared with existing drugs in terms of high malarial activity and cytotoxicity.

BEST MODE OF CARRYING OUT THE INVENTION

The first aspect of the present invention relates to a compound with antimalarial activity. The compound with antimalarial activity is represented by the following chemical formula.

[Chemical Formula 12]

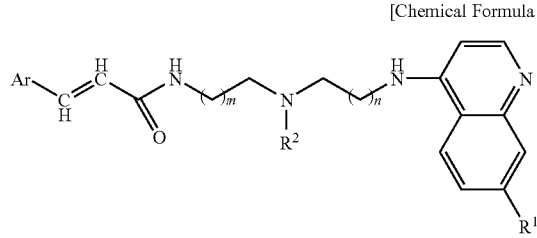

wherein R1 is H, Cl or $OCH_3$; R2 is H or $CH_3$; Ar is imidazole, triazole, pyridine, benzene, pyrrole, furan, thiophene or derivatives thereof; n is 1 to 5; and m is 1 to 5.

[Chemical Formula 13]

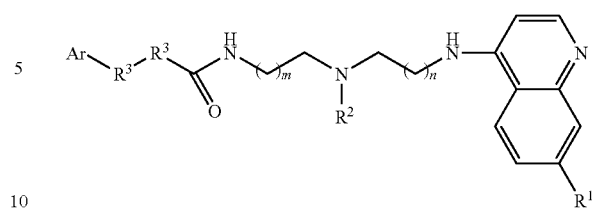

wherein R1 is H, Cl or $OCH_3$; R2 is H or $CH_3$; R3 is $CH_2$, $CH(CH_3)$ or $C(CH_3)_2$; Ar is imidazole, triazole, pyridine, benzene, pyrrole, furan, thiophene or derivatives thereof; n is 1 to 5; and m is 1 to 5.

As is apparent from the above-mentioned chemical formula, the compound with antimalarial activity of the present invention has a structure in which a conjugated molecule is introduced into a quinoline ring via a linker and interacts with heme strongly. Thus, high antimalarial activity is exhibited.

Herein, it is preferable that when the compound with antimalarial activity is used as an active ingredient of medicine (i.e., an antimalarial drug), it is preferable that the compound has a low molecular weight considering pharmacokinetics. Therefore, the numerical values of n and m are small. The n and m are preferably in the range from 1 to 3; and more preferably 1 or 2. Furthermore, it is preferable that n and m are equal to each other, so that amine as a linker has a symmetric property. With this design, when the below-mentioned two-stage synthesis is carried out, two different kinds of synthesized products having different linking modes of amine are not produced, which is therefore advantageous in synthesis.

One exemplary embodiment of the present invention is a compound with antimalarial activity represented by the following chemical formula.

[Chemical Formula 14]

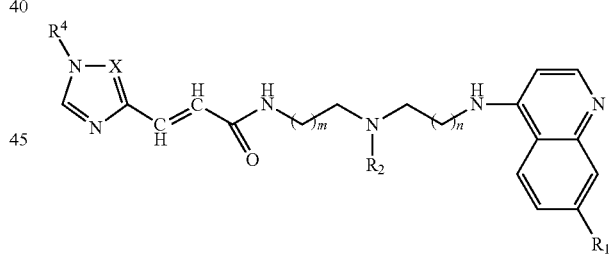

wherein R1 is H, Cl or $OCH_3$; R2 is H or $CH_3$; R4 is H or $CH_3$; X is CH or N; n is 1 to 5; and m is 1 to 5.

A specific example of compounds includes the following compounds. Note here that the detail of synthesizing methods and activity evaluations of these compounds are mentioned below.

(1) A compound represented by the chemical formula, wherein R1 is Cl; R2 is $CH_3$; R3 is CH; R4 is H; X is CH; n is 1; and m is 1.

(2) A compound represented by the chemical formula, wherein R1 is Cl; R2 is $CH_3$; R3 is CH; R4 is H; X is CH; n is 2; and m is 2.

One exemplary embodiment of the present invention is a compound with antimalarial activity represented by the following chemical formula.

[Chemical Formula 15]

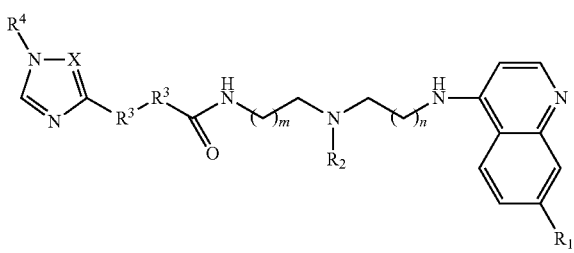

wherein R1 is H, Cl or OCH$_3$; R2 is H or CH$_3$; R3 is CH$_2$, CH(CH$_3$) or C(CH$_3$)$_2$; R4 is H or CH$_3$; X is CH or N; n is 1 to 5; and m is 1 to 5.

A specific example of compounds includes the following compounds. Note here that the detail of synthesizing methods and activity evaluations of these compounds are mentioned below.

(3) A compound represented by the chemical formula, wherein R1 is Cl; R2 is CH$_3$; R3 is CH$_3$; R4 is H; X is CH; n is 1; and m is 1.

(4) A compound represented by the chemical formula, wherein R1 is Cl; R2 is CH$_1$; R3 is CH$_2$; R4 is H, X is CH; n is 2; and m is 2.

Another aspect of the present invention relates to an antimalarial drug containing the above-described compound with antimalarial activity or salts thereof as an active ingredient. Herein, the kinds of the salts are not particularly limited as long as they are pharmaceutically acceptable. An example of the salts may include a salt with hydrochloric acid, phosphoric acid, sulfuric acid, nitric acid, boric acid, and the like (inorganic acid salt); and a salt with formic acid, acetic acid, lactic acid, fumaric acid, maleic acid, tartaric acid, citric acid, and the like (organic acid salt). Preparation of such salts can be carried out by a routine means.

The active ingredient can be formulated according to usual methods. In formulation, other pharmaceutically acceptable components (for example, carriers, vehicles, disintegrators, buffers, emulsifying agents, suspensions, soothing agents, stabilizers, preservatives, antiseptic agents, physiologic saline, and the like) can be contained. An example of vehicles may include lactose, starch, sorbitol, D-mannitol, sucrose, and the like. An example of disintegrators may include starch, carboxymethyl cellulose, calcium carbonate, and the like. An example of buffers may include phosphate, citrate, acetate, and the like. An example of emulsifying agents may include gum Arabic, sodium alginate, traganth, and the like. An example of suspensions may include glyceryl monostearate, aluminium monostearate, methyl cellulose, carboxymethyl cellulose, hydroxymethyl cellulose, sodium lauryl sulfate, and the like. An example of soothing agents may include benzyl alcohol, chlorobutanol, sorbitol, and the like. An example of stabilizers may include propylene glycol, diethylene sulfite, ascorbic acid, and the like. An example of preservatives may include phenol, benzalkonium chloride, benzyl alcohol, chlorobutanol, methylparaben, and the like. An example of antiseptic agents may include benzalkonium chloride, parahydroxy benzoic acid, chlorobutanol, and the like.

Formulation forms are not particularly limited and may be formulated in a form of, for example, tablets, powders, fine granules, granules, capsules, syrup, injections, external preparation, suppository, and the like.

The thus formulated drugs of the present invention can be administered to subjects by oral administration or parenteral administration (intravenous, intra-arterial, subcutaneous, muscular, intraperitoneal injections, and the like) according to the forms. The "subjects" herein are not particularly limited and include human and non-human mammalians (including pet animals, domestic animals, and laboratory animals, and specifically including, for example, mouse, rat, guinea pig, hamster, monkey, cow, pig, goat, sheep, dog, cat, chicken, quail, and the like.). Preferably, the antimalarial drug of the present invention is applied to human.

The content of the active ingredient in the antimalarial drug of the present invention generally differs depending upon the formulation forms, but it is, for example, about 0.001 wt. % to about 90 wt. % so that a desired dosage amount can be achieved.

Another aspect of the present invention provides a prevention method or a treatment method for malaria (hereinafter, referred to as "treatment method and the like" by combining these both methods) using the above-mentioned antimalarial drug. The treatment method and the like of the present invention include a step of administering the antimalarial drug of the present invention to a living body. Administration routes are not particularly limited, and may include oral, intravenous, intradermal, subcutaneous, intramuscular, intraperitoneal, transmucosal administrations, and the like. Such administration routes are not exclusive to each other but may be used in combination of two or more thereof (for example, at the same time or a predetermined time after oral administration, intravenous injection may be carried out). Note here that oral administration is preferred because administration can be carried out easily.

The dosage amount of the antimalarial drug varies depending upon symptoms, and age, sex, and body weight of subjects. The person skilled in the art can determine an appropriate dosage amount properly. For example, the dosage amount can be set so that the amount of the active ingredient is about 1 to 1000 mg/day, and preferably about 20 to 500 mg/day when it is administered to an adult subject (body weight: about 60 kg). As administration schedule, for example, the drugs are administered once to several times a day, once in two days, or once in three days, and the like. The administration schedule can be determined by considering conditions of subjects or the efficacy duration time of the drugs.

EXAMPLES

1. Design of Compound with Antimalarial Activity

Heme generated in the phagocytosis of erythrocyte by parasitic protozoa is accumulated in the parasitic protozoa and acts as a harmful material to the parasitic protozoa. Parasitic protozoa convert heme into hemozoin so as to detoxify heme. It is estimated that a quinoline antimalarial drug is linked to heme by way of formation of ion pair and stacking interaction so as to inhibit the polymerization of heme. Noted to this point, design shown in FIGS. 2 and 3 are carried out in order to create an antimalarial drug having a strong action by the extremely high heme affinity. That is to say, interaction with heme is enhanced by introducing a molecule having a π-plane carrying out a π-π interaction with heme into a quinoline ring via a material such as amine having a positive charge (FIG. 2), or by introducing heterocycle and the like capable of being coordinated to heme iron in one side (FIG. 3). As one specific example based on this idea, design is carried out so that three different kinds of interactions with heme can be carried out simultaneously by placing an aliphatic amino group in a quinoline ring via a linker and further linking coordinating heterocycle such as imidazole, which is known to have a strong coordinating ability to heme, thereto via a linker (FIG. 4). Based on this design, below mentioned four kinds of new compounds are synthesized.

[Chemical Formula 16]

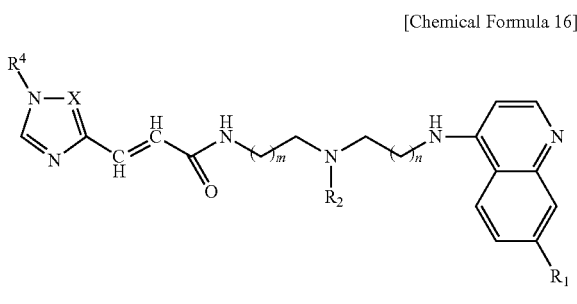

Compound 1

(N-(2-{[2-(7-Chloro-quinolin-4-ylamino)ethyl] methylamino}ethyl)-3-(1H-imidazol-4-yl)acrylamide)

In the above formula, R1 is Cl; R2 is $CH_3$; R4 is H; X is CH; n is 1; and m is 1.

Compound 2

(N-(3-{[3-(7-Chloro-quinolin-4-ylamino)propyl] methylamino}propyl)-3-(H-imidazol-4-yl)acrylamide)

In the above formula, R1 is Cl; R2 is $CH_3$, R4 is H; X is CH; n is 2; and m is 2.

[Chemical Formula 17]

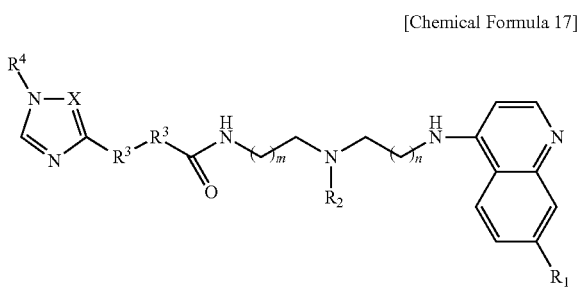

Compound 3

(N-(2-{[2-(7-Chloro-quinolin-4-ylamino)ethyl] methylamino}ethyl)-3-(1H-imidazol-4-yl)propionamide)

In the above formula, R1 is Cl; R2 is $CH_3$; R3 is $CH_3$; R4 is H; X is CH; n is 1; and m is 1.

Compound 4

(N-(3-{[3-(7-Chloro-quinolin-4-ylamino)propyl] methylamino}propyl)-3-(1H-imidazol-4-yl)propionamide)

In the above formula, R1 is Cl; R2 is $CH_3$; R3 is $CH_2$; R4 is H, X is CH; n is 2; and m is 2.

In these compounds a quinoline skeleton is linked to an imidazole structure having a strong coordinating ability to heme iron by using amines as a linker. These compounds are expected to exhibit high affinity by carrying out three different kinds of interactions with heme. Then, the antimalarial activities of these compounds are examined as follows.

2. Synthesis of a Novel Compound (1) Preparation of 3-(1H-Imidazol-4-yl)propionic acid (FIG. 5)

Urocanic acid (3-(1H-imidazol-4-yl)-acrylic acid) (138 mg, 1 mmol) was placed in a round-bottom flask and dist MeOH was added thereto until urocanic acid was completely dissolved. To this solution, 10% Pd/C (30 mg) was added, replaced with $H_2$ and stirred. After five hours, the loss of raw materials was confirmed, filtered, and the filtrate was concentrated under a reduced pressure to give the objective product.

(2) Preparation of amino quinoline (FIGS. 6(a) and 7(a))

As raw materials, 4,7-dichloroquinoline and triamins having different carbon chain lengths were used and stirred in the absence of solvent at 70° C. As a result, aminoquinoline (2Q) in which n is 2 and aminoquinoline (3Q) in which n is 3 were obtained at yields of 57% and 50% m, respectively. At this time, 2BQ was obtained at a yield of 19% and 3BQ was obtained at a yield of 18%.

(3) Synthesis of N-(2-{[2-(7-Chloro-quinolin-4-ylamino)ethyl]methylamino}ethyl)-3-(1H-imidazol-4-yl)acrylamide: (uro-2Q) (FIG. 6(b)).

Urocanic acid (138 mg, 1 mmol) was dissolved in dist THF, and a condensing agent CDI (200 mg, 1.3 mmol) was added to this solution. The solution was stirred. After two hours, 2Q (278 mg, 1 mmol) dissolved in dist THF was added and continued to be stirred. After reaction overnight, the reaction solution was filtered through a Kiriyama funnel. The filtrate was concentrated under a reduced pressure to give a yellow oil and this oil was purified by HPLC. Yield: 31%.

(4) Synthesis of N-(3-{[3-(7-Chloro-quinolin-4-ylamino)propyl]methylamino}propyl)-3-(1H-imidazol-4-yl) acrylamide: (uro-3Q) (FIG. 6 (b))

Urocanic acid (138 mg, 1 mmol) was dissolved in dist THF, and a condensing agent CDI (200 mg, 1.3 mmol) was added to this solution. The solution was stirred. After two hours, 3Q (306 mg, 1 mmol) dissolved in dist THF was added and continued to be stirred. After reaction overnight, the reaction solution was filtered through a Kiriyama funnel. The filtrate was concentrated under a reduced pressure to give a yellow oil and this oil was purified by HPLC. Yield: 58%.

(5) Synthesis of N-(2-{[2-(7-Chloro-quinolin-4-ylamino)ethyl]methylamino}ethyl)-3-(1H-imidazol-4-yl)propionamide: (im-2Q) (FIG. 7 (b))

3-(1H-Imidazol-4-yl)propionic acid (140 mg, 1 mmol) was dissolved in dist THF, and a condensing agent CDI (200 mg, 1.3 mmol) was added to this solution. The solution was stirred. After two hours, 2Q (278 mg, 1 mmol) dissolved in dist THF was added and continued to be stirred. After reaction overnight, the reaction solution was filtered through a Kiriyama funnel. The filtrate was concentrated under a reduced pressure to give a yellow oil and this oil was purified by HPLC. Yield: 23%

(6) Synthesis of N-(3-{[3-(7-Chloro-quinolin-4-ylamino)propyl]methylamino}propyl)-3-(1H-imidazol-4-yl)-propionamide: (im-3Q) (FIG. 7 (b))

3-(1H-Imidazol-4-yl)propionic acid (140 mg, 1 mmol) was dissolved in dist THF, and a condensing agent CDI (200 mg, 1.3 mmol) was added to this solution. The solution was stirred. After two hours, 3Q (306 mg, 1 mmol) dissolved in dist THF was added and continued to be stirred. After reaction overnight, the reaction solution was filtered through a kiriyama funnel. The filtrate was concentrated under a reduced pressure to give a yellow oil and this oil was purified by HPLC. Yield: 44%

3. Evaluation of Synthesized Compounds

Firstly, the synthesized compounds are examined for a change of absorption spectrum of a porphyrin ring and heme affinity is studied. As a result, it is suggested that the synthesized compounds show stronger affinity than existing drugs and that one molecule interacts with 3-4 equivalents of heme (not shown). Subsequently, the antimalarial activity and the cytotoxicity are examined by the following methods, respectively.

(1) Evaluation Method of Antimalarial Activity

Human erythrocyte infected with malaria parasite (*Plasmodium falciparum* (ATCC 30932, FCR-3 strain)) is prepared on a 24-well culture plate and 5 µl each of DMSO solutions of antimalarial drug candidate compounds prepared at various concentrations is added. Thereafter, the erythrocyte is cultured at 37° C. for 72 hours. A part of the cultured erythrocyte is subjected to Giemsa staining. Then, the number of cells infected with malaria is counted under microscope. $EC_{50}$ values are calculated based on the measurement values.

(2) Evaluation Method of Cytotoxicity (See Hye-Sook Kim; Yasuharu Shibata; Yusuke Wataya; Kaoru Tsuchida; Araki Masuyama; Masatomo Nojima. J. Med. Chem. 1999, 42, 2604-2609)

The concentration of human breast cancer cells (Mouse mammary tumor FM3A cells) is adjusted to $5\times10^4$ cells/ml, and 5 µl of DMSO solutions of antimalarial drug candidate compounds prepared at various concentrations is added. The cells area cultured at 37° C. for 48 hours and then, the number of surviving cells is counted by the use of microcell counter CC-130 (To a Medical Electric Co.). The measurement results are compared with the results obtained from the control experiment so as to calculate $EC_{50}$ value.

(3) Evaluation Results

The evaluation results of the respective compounds are shown in FIG. 8. As shown from FIG. 8, antimalarial activities of the synthesized compounds show superior values as compared with existing drugs. Furthermore, the cytotoxicity of the synthesized compounds is low as a whole. It is determined that the synthesized compounds have lower toxicity than that of any existing drugs. When a comparison is carried out based on the selectivity that is an important factor for reducing adverse effects, uro-2Q shows a value that greatly exceeding that of the existing drugs. Furthermore, the selectivity of uro-3Q is also the same as chloroquine and higher than the other existing drugs.

4. Conclusion

By carrying out design that considers the intermolecular interaction, a compound having both antimalarial activity and high selectivity can be synthesized successfully. In particular, since uro-2Q has higher antimalarial activity and lower toxicity as compared with existing drugs, it is expected to be a lead medicine with a wide margin of safety.

INDUSTRIAL APPLICABILITY

A compound with antimalarial activity of the present invention is a compound obtained by linking a quinoline skeleton to a conjugated molecule (a molecule having a n-plane carrying out a π-π interaction with heme, heterocycle capable of being coordinated to heme iron, or the like) by a linker. The compound has a high affinity and exhibits an excellent antimalarial activity. An antimalarial drug containing such a compound with antimalarial activity is very useful for prevention and treatment of malaria.

The present invention is not limited to the description of the above exemplary embodiments and Examples. A variety of modifications, which are within the scopes of the following claims and which can be easily achieved by a person skilled in the art, are included in the present invention.

Contents of the theses, Publication of Patent Applications, Patent Publications, and other published documents referred to in this specification are herein incorporated by reference in its entity.

The invention claimed is:

1. A compound with antimalarial activity represented by the following formula:

[Chemical Formula 1]

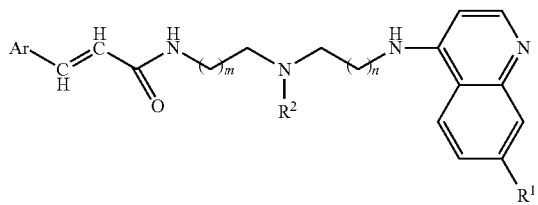

wherein R1 is H, Cl or $OCH_3$; R2 is H or $CH_3$; Ar is imidazole, triazole, pyridine, benzene, pyrrole, furan, thiophene or derivatives thereof; n is 1 to 5; and m is 1 to 5.

2. The compound with antimalarial activity according to claim 1, which is represented by a following chemical formula:

[Chemical Formula 2]

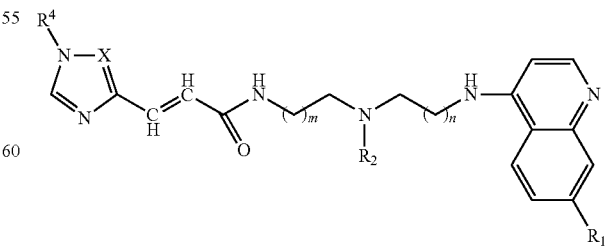

wherein R1 is H, Cl or $OCH_3$; R2 is H or $CH_3$; R4 is H or $CH_3$; X is CH or N; n is 1 to 5; and m is 1 to 5.

3. The compound with antimalarial activity according to claim 2, which is:
(1) a compound represented by the chemical formula, wherein R1 is Cl; R2 is $CH_3$; R4 is H; X is CH; n is 1; and m is 1; or,
(2) a compound represented by the chemical formula, wherein R1 is Cl; R2 is $CH_3$; R4 is H; X is CH; n is 2; and m is 2.

4. An antimalarial drug comprising a compound with antimalarial activity according to claim 1, or pharmaceutically acceptable salts thereof as an active ingredient.

5. A method of treating malaria, comprising administering an antimalarial drug according to claim 4 to a subject.

6. An antimalarial drug comprising a compound with antimalarial activity according to claim 2, or pharmaceutically acceptable salts thereof as an active ingredient.

7. An antimalarial drug comprising a compound with antimalarial activity according to claim 3, or pharmaceutically acceptable salts thereof as an active ingredient.

8. A method of treating malaria, comprising administering an antimalarial drug according to claim 6 to a subject.

9. A method of treating malaria, comprising administering an antimalarial drug according to claim 7 to a subject.

\* \* \* \* \*